United States Patent [19]

Williams et al.

[11] 4,294,853
[45] Oct. 13, 1981

[54] BIOCIDAL ADDITIVE FOR CUTTING FLUIDS

[75] Inventors: John W. Williams, Vallejo, Calif.; Robert A. Smith, Lindenhurst; Francis W. Arbir, Itasca, both of Ill.

[73] Assignee: Abbott Laboratories, North Chicago, Ill.

[21] Appl. No.: 156,141

[22] Filed: Jun. 3, 1980

Related U.S. Application Data

[63] Continuation-in-part of Ser. No. 48,202, Jun. 13, 1979, abandoned.

[51] Int. Cl.$^3$ ............................................. A01N 37/12
[52] U.S. Cl. ................................. 424/319; 106/18.34; 106/18.35; 252/45; 252/47.5; 424/337
[58] Field of Search ............................. 106/18.34, 18.35; 252/45, 47.5; 424/337, 319

[56] References Cited

U.S. PATENT DOCUMENTS

| | | | |
|---|---|---|---|
| 3,072,529 | 1/1963 | Sanders et al. | 424/365 |
| 3,615,745 | 10/1971 | Crovetti et al. | 424/337 |
| 3,663,623 | 5/1972 | Crovetti et al. | 260/607 A |
| 4,018,611 | 4/1977 | Cramer et al. | 106/18.32 |

OTHER PUBLICATIONS

Izzat et al., "The Potentiation of the Antimicrobial Activities of Cutting Fluid Preservatives by EDTA", ASLE Preprint, Apr. 1978.

*Primary Examiner*—Lorenzo B. Hayes
*Attorney, Agent, or Firm*—Robert L. Niblack; Paul D. Burgauer

[57] ABSTRACT

The addition of a combination of $CH_3SO_2CHI_2$ and certain chelating agents to cutting fluid prevents bacterial and fungal growth. Concentrated aqueous co-dispersions thereof are particularly useful.

12 Claims, No Drawings

BIOCIDAL ADDITIVE FOR CUTTING FLUIDS

BACKGROUND OF THE INVENTION

This application is a continuation-in-part of our previously filed application, Ser. No. 048,202 filed June 13, 1979, now abandoned.

DETAILED DESCRIPTION OF THE INVENTION

In most instances involving commercial metal-cutting, the use of a cutting fluid is required. A cutting fluid is an aqueous system containing an additive, the cutting oil, which serves as a heat transfer agent, corrosion inhibitor and lubricant in the cutting operation. Cutting oils may be either emulsifiable oils, straight oils or synthetic oils. They are added to water at ratios of 1–5 parts by volume to 100 parts water. Large volumes of such fluids are required to serve properly as a heat transfer fluid, and for reasons of economy and potential pollution problems resulting from its discharge, recirculation of this fluid is required. This, in turn, requires that the fluid does not spoil due to biological attack during use or during storage.

While metal deposits can easily be removed from the recirculating fluid by mechanical means, bacterial and fungal contaminants represent more serious difficulties; they could easily ruin an entire system of recirculating cutting fluid which otherwise could be used for months. In order to prevent microbial degradation, the metal cutting industry requires additives that inhibit the growth of bacteria and/or the growth of fungi in the aqueous environment of this fluid. Such an additive is preferably available as a concentrated stock liquid which dissolves or disperses easily in the metal cutting fluid; it must not be corrosive to the metallic environment of its storage, circulation and operating area.

It has now been found that a combination of one part of the known fungicide, 1,1-diiododimethyl sulfone (hereinafter called DIDS) and 0.5–250 parts by weight of a chelating agent of the formula:

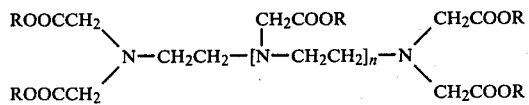

wherein R is hydrogen, an alkali metal cation or ammonium, and n is 0 or 1, inhibits, at low concentrations, both industrial bacterial and fungal growth for extended periods of time. These new mixtures are not corrosive and can be stored as concentrated aqueous codispersions. The new combination is useful in all of the above-named types of cutting oils. Typical representatives of the above chelating agents are the disodium salt of ethylenediamine tetraacetic acid (hereinafter named EDTA), disodium salt, Versene (=EDTA tetrasodium salt), diethylenetriaminepentaacetic acid (DTPA), or the corresponding ammonium or potassium salts and the like.

The new combination fungicide has unique advantages over a chelating agent alone or DIDS alone, for instance, EDTA or its salts alone are essentially inactive and high concentrations are required to produce biocidal effects while DIDS is costly and quite toxic. EDTA and DTPA and their salts have been found to be unique and surprisingly outstanding potentiators for the desirable and useful protective activity of DIDS in cutting fluids. By their addition, the necessary amount of DIDS can be cut to 50% to produce equal or better biocidal effects than DIDS alone.

The components used in the present invention are well known materials: The above chelating agents have been known for decades and DIDS is known from U.S. Pat. No. 3,615,745. The named patent mentions the fungicidal and bactericidal activity of DIDS with reference to certain substrates. However, prevention of bacterial or fungal growth in metal cutting fluids is a much more difficult task. It has been recognized for many years that only very few biocides are suitable in metal working fluids and that only very few chelating agents have the ability to potentiate the activity of selected biocides.

The activity of the new combination of DIDS/chelate against industrial micro-organisms is particularly unusual, as only an extremely small number of compounds tested in metal working fluids prove to be active against both bacteria and fungi and most biocides useful in other industrial or agricultural substrates fail in cutting fluids.

In order to show the use of the above combination of materials, reference is made to the following examples which, however, serve only as illustration and are not meant to limit the invention in any respect.

EXAMPLE 1

To establish the activity of the above combination against various industrial bacteria and fungi, the minimum inhibitory concentrations (MIC) were determined in various cutting fluids. A bacterial and fungal mixture containing Pseudomonas, E. coli, Paracolobactrum, Proteus, Klebsiella and Aerobacter (the more common bacteria found in cutting fluids) and Fusarium, Cephalosporium and Cladosporium (the most common fungi found in cutting fluids) was used in this test. The bacteria-fungi mixture was placed in a test tube in two industrial cutting oils and then diluted with water to the commercially used oil/water ratio of 1:40. The oils used were A a petroleum-based coolant (Sun-Seco, marketed by the Sun Oil Co.) and B a synthetic coolant (Trim Regular, marketed by Master Chemical Co.). The results are tabulated in Table I.

TABLE I

| Materials Tested | MIC(A) | MIC(B) |
| --- | --- | --- |
| DIDS | 15 ppm | 7 ppm |
| EDTA | >125 ppm | >125 ppm |
| DIDS/EDTA | 8/48 ppm | 4/24 ppm |

These figures show that only about half of the amount of DIDS is required when it is used in combination with a typical chelating agent.

EXAMPLE 2

In a synergism study, using the standardized microtiter technique, Aerobacter and Pseudomonas were added to the nutrient broth at 10,000 colony-forming units/ml. of each. The MIC (in ppm) of various chelators and their combinations with DIDS were determined and tabulated below:

TABLE II

| Chelate | MIC of Chelate Alone | MIC of Combination (DIDS/Chelate) |
| --- | --- | --- |
| Versene powder | 500 ppm | 1.5/100 ppm |

TABLE II-continued

| Chelate | MIC of Chelate Alone | MIC of Combination (DIDS/Chelate) |
|---|---|---|
| Versene liquid | 1000 ppm | 6/400 ppm |
| EDTA . 2Na | 1000 ppm | 6/100 ppm |
| DPTA | 2000 ppm | 0.8/200 ppm |
|  |  | 1.5/100 ppm |
|  |  | 3/100 ppm |
| EDTA . 2NH$_4$ | >2000 ppm | 3.9/500 ppm |

Since DIDS alone has an MIC of 12.5 ppm, the above results indicate ½ to ⅛ of DIDS can be used with the appropriate amount of a chelating agent.

EXAMPLE 3

DIDS/chelate mixtures were also tested at various concentrations and ratios in oils A and B (identified in Example 1) under simulated industrial use conditions. The results expressed in days of protection are given in Table III.

TABLE III

| Concentrations (ppm/Days) of Inhibition | | | |
|---|---|---|---|
| DIDS | EDTA . 2Na | in Trim | in Sun-Seco |
| 1020 |  | 35 | >105 (1) |
| 510 |  | 7 | >105 (1) |
| 382.5 |  | 28 | 42 |
| 255 |  | 42 | 35 |
| 127.5 |  | 35 | 28 |
| 63.75 |  | 21 | 21 |
| 0 |  | 0 | 0 |
| 765 | 250 | 28 | >105 (1) |
| 510 | 500 | 56 | >105 (1) |
| 255 | 750 | 63 | >105 (1) |
| 0 | 1000 | 28 | 14 |

(1) Test was terminated after 105 days.

In this test, DIDS was used as a 51% solution in DMF and the chelating agent was simultaneously added to the cutting fluid as a solid. Results with other organic solvents for DIDS are found to be similar. Also, the use of DIDS plus chelates in other oils gives similar results, e.g., cutting oils sold by Shamrock, Norton, Quaker, Texaco or those sold as Do All, IRMCO, Polar Chip, Shercool, etc.

EXAMPLE 4

The following tests were carried out in the fashion of Example 3 using 1 volume of a commercial cutting oil in 40 volumes of aqueous cutting fluid. The oils are identified only as to their commercial source; the biocides are made up using the following ingredients (by weight):
I. 40% EDTA.2Na + 14.5% DIDS
II. 42.32% DTPA + 5.28% DIDS
III. 48% DIDS alone Table IV shows the number of weeks the above mixtures provide protection at the concentrations listed. Again, the tests were discontinued after 15 weeks (105 days).

TABLE IV

| Oil Formulation | Quaker | | | Vantrol | | | Sun-Seco | | | Texaco-591 | | |
|---|---|---|---|---|---|---|---|---|---|---|---|---|
|  | I | II | III | I | II | III | I | II | III | I | II | III |
| 150 ppm |  | 7 |  |  | 1 |  |  | 2 |  |  |  | 2 |
| 300 ppm |  | 9 |  |  | 3 |  |  | 3 |  |  |  | 5 |
| 450 ppm | 5* | 9 | 2* |  | 3 | 5* |  | 5 | 2* |  |  | 5 |
| 600 ppm |  | 15 |  |  | 5 |  |  | 6 |  |  |  | 7 |
| 800 ppm |  | 15 |  |  | 5 |  |  | 6 |  |  |  | 7 |
| 1000 ppm | 5 | 7 | 15 | 4 | 9 | 10 | 15 | 15 | 6 | 15 | 9 | 7 |
| 1500 ppm | 15 |  | 15 | 9 |  | 15 | 15 |  | 15 |  |  | 7 |
| 2000 ppm | 15 | 15 | 15 | 15 | 15 | 15 | 15 | 15 | 15 | 15 | 15 | 8 |

*500 ppm instead of 450 ppm.

The results listed in Table IV clearly show that with a chelate, the actual concentration of DIDS to get biocidal protection is far below the amount required when DIDS is used alone.

It is easily seen from the tables that the combination of a chelating agent with DIDS greatly improves the performance of DIDS. For instance, 255 ppm of DIDS protects Trim and Sun-Seco oils in cutting fluids for only 6 or 5 weeks, respectively, while the addition of potentiator disodium EDTA produces protection for 9 to 15 weeks, respectively.

Compositions most practical for use by the consumer are the above described concentrates containing between 10 and 60% by weight of the combination of DIDS and a chelating agent. An excellent concentrate can be prepared by combining 12 parts of DIDS, 36 parts of a chelating agent, 5.33 parts of silica, 1 part of a wetting agent, 4 parts ethylene glycol, 3 parts of a nonionic surfactant, a trace of a defoamer and 39.3 parts of water. These materials are first mixed and then dispersed in a roller mill, a ball, pebble or sand mill, or a kinetic-energy disperser. Such liquid compositions are easily dispersed in water, they are stable for extended storage periods, and they are compatible with cutting oils commercially used on a large scale. However, other water soluble, organic, noncorrosive liquids may sometimes be added because of other beneficial properties they may have. Typical examples thereof are DMF, DMAc or N-methylpyrrolidone, which in some instances add to the lubricating qualities of the cutting fluid. Others may be more compatible with the one or the other of the frequently used commercial cutting oils. Where the above chelating agent is a salt of DTPA, a particularly stable composition is obtained.

We claim:

1. A mixture for use as a biocidal additive to industrial cutting fluids consisting essentially of 1 part by weight of 1,1-diiododimethyl sulfone and between 0.5 and 250 parts by weight of a chelating agent $$\begin{array}{c} ROOCCH_2 \\ \diagdown \\ N-CH_2CH_2-[N-CH_2CH_2]_n-N \\ \diagup \quad | \quad \diagdown \\ ROOCCH_2 \quad CH_2COOR \quad CH_2COOR \\ \quad \quad \quad \quad \quad \quad \quad \quad \quad \quad CH_2COOR \end{array}$$

wherein R is hydrogen, an alkali metal cation or ammonium, and n is 0 or 1.

2. The mixture of claim 1 wherein said chelating agent is a salt of ethylenediamine tetraacetic acid.

3. The mixture of claim 2 wherein said salt is the diammonium salt.

4. The mixture of claim 2 wherein said salt is the tetrasodium salt.

5. The mixture of claim 2 wherein said salt is the disodium salt.

6. The mixture of claim 1 wherein said chelating agent is diethylenetriamine pentaacetic acid.

7. A stable, liquid composition for dissolution in a metal working fluid to protect such fluid against common industrial micro-organisms containing between 10 and 60% by weight of the combination of 1 part by weight of 1,1-diiododimethyl sulfone and 0.5–250 parts by weight of the chelating agent defined in claim 1, homogeneously dispersed in water.

8. The composition of claim 7 wherein said chelating agent is a salt of ethylenediamine tetraacetic acid.

9. The composition of claim 8 wherein said salt is the tetrasodium salt.

10. The composition of claim 8 wherein said salt is the diammonium salt.

11. The composition of claim 8 wherein said salt is the disodium salt.

12. The composition of claim 7 wherein said chelating agent is diethylenetriamine pentaacetic acid.

* * * * *